United States Patent [19]

Kunnen et al.

[11] Patent Number: 6,025,528
[45] Date of Patent: *Feb. 15, 2000

[54] AQUEOUS METHOD TO PREPARE CYCLOPROPYL METHYLKETONE FROM ACETYL-PROPANOL

[75] Inventors: Kevin Kunnen; Ignacio H. Sanchez, both of Lafayette, Ind.

[73] Assignee: Great Lakes Chemical Corporation, West Lafayette, Ind.

[*] Notice: This patent issued on a continued prosecution application filed under 37 CFR 1.53(d), and is subject to the twenty year patent term provisions of 35 U.S.C. 154(a)(2).

[21] Appl. No.: 09/033,762

[22] Filed: Mar. 3, 1998

[51] Int. Cl.$^7$ .................................................. C07C 45/45
[52] U.S. Cl. .............................................. 568/392
[58] Field of Search ............................. 568/392

[56] References Cited

U.S. PATENT DOCUMENTS

| | | | |
|---|---|---|---|
| 4,206,230 | 6/1980 | Paul ........................................ | 424/304 |
| 4,686,291 | 8/1987 | Lantzsch et al. ....................... | 544/335 |
| 5,157,048 | 10/1992 | Mills et al. ............................. | 549/498 |
| 5,254,739 | 10/1993 | Hunston et al. ........................ | 568/346 |
| 5,274,136 | 12/1993 | Mills et al. ............................. | 514/461 |
| 5,629,455 | 5/1997 | Kaufhold et al. ...................... | 568/346 |
| 5,763,627 | 6/1998 | Kaufhold ................................ | 549/507 |

OTHER PUBLICATIONS

Freer and Perkin: Synthetical Formation of Closed Carbon–Chains, pp. 820–853.
George W. Cannon, et al.: Methyl Cyclopropyl Ketone.
Chemistry Letters. Aklylation Reaction Accompanied by Dealkoxycarbonylation of B–Keto Esters, Geminal Diesters and Cyano Ester in Hexamethylphosphoric Triamide (HMPA) Tetrahedron Letters, Takei and Kawano, pp. 4389–4392, 1975 A Novel synthesis of Cyclopropyl Ketones Via Decarboxylative Ring Contractions of a–Acyl–Butyrolactones Catalyzed by Halide Ions in Dipolar Aprotic Solvents.
*J. Org. Chem.*, vol 40, No. 20, 1975, Singh and Danishefsky, Preparation of Activated Cyclopropanes by Phase Transfer Alkylation.
Bulletin de la Societe Chimique de Belgique, Nov. 1927, Contribution a l'ende des Composes Cycliques Trimethylenquies (French).
Contribution a l'etude des composes cycliques trimethyleniques du type, par M. Pierre Bruylants.
Morrison et al., Organic Chemistry, 2nd Edn., pp. 529–531, 1966.

*Primary Examiner*—James H. Reamer
*Attorney, Agent, or Firm*—Woodard, Emhardt, Naughton, Moriarty & McNett Patent and Trademark Attorneys

[57] ABSTRACT

An entirely aqueous method to prepare cyclopropyl methylketone from acetyl-propanol. The method is practiced by (1) forming a mixture of acetyl-propanol and an aqueous hydrogen halide, (2) distilling the mixture and returning at least a portion of the distillate that is aqueous to the distilland, (3) recovering 5-halo-2-pentanone from the distillate, and (4) reacting the 5-halo-2-pentanone with a basic solution that is from about 1-wt % to about 25-wt % base and about 75-wt % to about 99-wt % water to yield cyclopropyl methylketone.

24 Claims, No Drawings

AQUEOUS METHOD TO PREPARE CYCLOPROPYL METHYLKETONE FROM ACETYL-PROPANOL

Our invention generally relates to a process to make cyclopropyl methylketone from acetyl-propanol, and more particularly relates to a process that makes high-purity cyclopropyl methylketone without an organic solvent.

I. BACKGROUND OF THE INVENTION

Cyclopropyl methylketone is used to manufacture a variety of agricultural chemicals and pharmaceuticals. One route to prepare this compound begins with α-acetyl-γ-butyrolactone. In this process, 5-chloro-2-pentanone is first formed by reacting the α-acetyl-γ-butyrolactone with an acid. This intermediate is then isolated by ether extraction and reacted with 50-wt % aqueous sodium hydroxide. This second reaction forms cyclopropyl methylketone, which is then purified by distillation. See Cannon, G. W.; Ellis, R. C.; and Leal, J. R., *Org. Synth. Coll.*, Vol. IV, p. 597.

Another route to prepare cyclopropyl methylketone also begins with α-acetyl-γ-butyrolactone. In this process, the cyclopropyl methylketone is formed directly by heating α-acetyl-γ-butyrolactone in the presence of a halide salt, and preferably an organic solvent. See U.S. Pat. No. 5,254,739 to Hunston and others.

The problem with these and other methods is that they are impractical on a large scale. High concentrations of base are expensive and require special handling techniques. Organic solvents are difficult, if not impossible, to discard under current EPA regulations, and typically must be recovered with distilling operations. As a result, what is needed is a more economical process to prepare cyclopropyl methylketone, and this invention addresses that need.

II. SUMMARY OF THE INVENTION

One form of this invention is a method to prepare cyclopropyl methylketone from acetyl-propanol in the absence of an organic solvent. In a first method, acetyl-propanol is reacted with an aqueous hydrogen halide to produce an intermediate. The intermediate is then reacted with a basic solution that is preferably from about 1-wt % to about 25-wt % base and about 75-wt % to about 99-wt % water to produce cyclopropyl methylketone.

Another form of this invention is a method to prepare cyclopropyl methylketone by (1) forming a mixture of acetyl-propanol and an aqueous hydrogen halide, (2) distilling the mixture and returning at least a portion of the distillate that is aqueous to the still pot and, (3) recovering 5-halo-2-pentanone from the distillate, and (4) reacting the 5-halo-2-pentanone with a basic solution that is from about 1-wt % to about 25-wt % base and about 75-wt % to about 99-wt % water.

An object of this invention is to provide an economically viable process to manufacture large amounts of high quality cyclopropyl methylketone.

An advantage of this invention is that it does not require an organic solvent to extract impurities from the intermediate or the final product.

Another advantage of this invention is that, when compared to similar methods, it produces a higher quality product while using lower concentrations of base.

A feature of this invention is that water is the only solvent that it requires.

Another feature of this invention is that it proceeds faster than methods that use higher concentrations of base.

III. DESCRIPTION OF THE PREFERRED EMBODIMENTS

Specific language is used in the following description and examples to publicly disclose the invention and to convey its principles to others. No limits on the breadth of the patent rights based simply on using specific language are intended. Also included in our rights are any alterations and modifications to the descriptions that should normally occur to one of average skill in this technology.

One aspect of this invention is a process to prepare the intermediate, 5-halo-2-pentanone. It is formed by contacting acetyl-propanol, also known as 5-hydroxy-2-propanone, with an aqueous hydrogen halide. Acetyl-propanol is widely known and commercially available from many sources such as the Aldrich Chemical Company, Inc., located in Milwaukee, Wis., U.S.A. Suitable hydrogen halides are also widely known and commercially available and are preferably used at a concentration from about 20-wt % to about 36-wt % with about 27-wt % being the most preferred. And particularly suitable halogen halides are hydrogen bromide and hydrogen chloride.

Suitable reactant weight ratios of hydrogen halide to acetyl-propanol are those sufficient to cause the substitution of the hydroxyl group on the propanone with a halogen. Examples of such ratios are those within the range of 4 equivalent weights of hydrogen halide to 1 equivalent weight of acetyl-propanol or 4:1 and down to 1:1, with about 3:1 being preferred.

Though acetyl-propanol and hydrogen halide react at room temperature, it is preferable that they are heated and distilled upon contact. When distilled, water and 5-halo-2-pentanone collect in the overhead condenser and separate into two distinct phases. The top organic phase contains 5-halo-2-pentanone and the bottom phase contains mostly water. Periodically or continuously, it is then preferable to return at least a portion of the bottom phase back to the reaction mixture. It has been discovered that the return increases the overall purity of the 5-halo-2-pentanone, which eliminates the need to extract any impurities with an organic solvent. When prepared in this fashion, the top organic phase will be 98% or higher 5-halo-2-pentanone.

A second aspect of this invention is a process to prepare cyclopropyl methylketone from 5-halo-2-pentanone, and is practiced by contacting the 5-halo-2-pentanone with a base. Most any base, organic or inorganic can be used, but inorganic bases are preferred. Example bases include such compounds as triethylamine, sodium hydroxide, and potassium hydroxide. The base should have an initial concentration that is something less than about 25-wt %, and is preferably from about 5-wt % to about 15-wt %, and even more preferably is about 10-wt %. It has been discovered that these relatively low concentrations allow the reaction to proceed considerably faster than those above 25-wt % will.

Suitable reactant weight ratios of base to 5-halo-2-pentanone are those sufficient to cause the cyclization of pentanone and eliminate the halogen. Examples of such ratios are those in a range of 1.5 equivalent weights of base to 1 equivalent weight of 5-halo-2-pentanone or 1.5:1 and down to 1:1, with about 1.2:1 being preferred.

The reaction begins when the compounds are mixed at room temperature, but it is preferable to maintain them between 30° C. and 40° C. throughout the reaction. Cyclopropyl methylketone will collect in the upper phase of the reaction vessel, and once separated, is preferably dried and distilled. The aqueous layer that remains may be recycled by adding additional base and combining the now recycled aqueous phase with additional 5-halo-2-pentanone. But preferably, only two recycles are performed on the initial charge of base, or in other words, only three batches of cyclopropyl methylketone are made from each initial charge of base. The crude CPMK will be about 95 to 97% pure before drying and distillation, and will be 99% or higher after drying and distillation.

IV. EXAMPLES

Example 1

Preparation of 5-Chloro-2-Pentanone. Acetyl-propanol (5,920 lbs., 54 lb.-moles), water (710 gallons), and 32% HCl (3 gallons, 0.3 lb.-moles) were charged into a 4,000 gallon GLS reactor. The resulting mixture was stirred for 1 hour. Thereafter, additional 32% HCl (1,975 gallons, 197.5 lb.-moles) was charged into the reactor and the mixture was heated to begin distillation. After 1,500 gallons of distillate had been collected and without stopping the distillation, 500 gallons of aqueous distillate were returned from the receiver to the reactor and the process continued. Distillate was returned at least three times over a period 10–13 hours. When 5-chloro-2-pentanone was no longer observed in the condensate stream, the distillation was terminated. Any aqueous phase remaining on the bottom of the receiver was transferred into the reactor and the 5-chloro-2-pentanone product was transferred into drums. Typically 12 drums (@400 lbs. per drum) and a heal drum were isolated (4,900 lbs. total, 40.7 pound moles), a 75% yield.

Example 2

10% Aqueous Sodium Hydroxide Preparation. For the initial base charge, sodium hydroxide 25% (262 gallons, 17.3 lb.-moles) and water (500 gallons) were charged into a 1,000 gallon GLS reactor and mixed.

Cyclopropyl Methylketone Production ("CPMK"). 5-Chloro-2-pentanone (1,600 lbs., 13.26 lb.-moles) was combined in the reactor with the initial charge of 10-wt % sodium hydroxide and the resulting mixture was stirred at 30–40° C. for 1 hour. Thereafter, stirring was terminated and the lower aqueous phase was transferred into another reactor for recycle. The crude CPMK layer left behind was then transferred into a 1,000 gallon GLS reactor for drying.

The lower aqueous phase was combined with flaked sodium hydroxide (640 lbs., 16 lb.-moles) and the above-described reaction was repeated with additional 5-chloro-2-pentanone. The CPMK produced from the recycled aqueous phase was again transferred for drying, and the lower aqueous phase was recycled a second time with additional sodium hydroxide to produce a third batch of 5-chloro-2-pentanone. After the third batch, the caustic phase was entirely replaced with a fresh charge of aqueous base, and the entire procedure was repeated.

Drying and Fractional Distillation. When five batches of crude CPMK, with or without a recycled forecut (discussed below) had been combined, they were dried over anhydrous calcium chloride (200 lbs.). An aqueous calcium chloride brine layer was separated from the drying vessel bottom and the dried CPMK (725–800 gallons) was transferred into a 1,000 gallon batch still for fractional distillation. 110 gallons of Norpar13®, a commercially available, high molecular weight, non-reactive high boiling chaser, was added to assist the distillation. The fraction collected between 23° C. and 90° C. (154 lbs.) was discarded as the purge cut. The purge cut contained mostly methyl tetrahydrofuran and acetone, which were impurities in the acetyl-propanol, and water. The forecut collected between 90° C. and 110° C. (915 lbs.) contained excessive amounts of water and was collected to dry and distill with the next batch of crude CPMK. The final cut collected between 110° C. and 116° C. (4,150 lbs., 49 lb.-moles) was the final product and produced a 73.6% yield (based on a 5,561 lb. CPMK charge).

Examples 3–7

The procedure in example 2 was repeated using 10-wt % base and 20-wt % base, and each was performed with (w/) and without (w/o) benzyltriethylammonium chloride to determine if a phase transfer catalyst had any effect on the reaction. [The kinetics of the four reactions are depicted in FIGS. 1 and 2.] The catalyst had no appreciable effect. But surprisingly, the lower the concentration of base, the faster the reaction proceeded.

V. THE CLAIMS

While the invention has been illustrated and described in detail, this is to be considered as illustrative and not restrictive of the patent rights. The reader should understand that only the preferred embodiments have been presented and that all changes and modifications that come within the spirit of the invention are included if the following claims or the legal equivalent of these claims describes them.

We claim:

1. A method to prepare cyclopropyl methylketone, comprising:
   (a) reacting acetyl-propanol with an aqueous hydrogen halide to produce an intermediate; and
   (b) reacting the intermediate with an aqueous base having a concentration in the range from about 1-wt % base to a concentration that is less than about 25-wt % base to produce cyclopropyl methylketone.

2. The method of claim 1, and where the aqueous base has a concentration from about 5-wt % to about 15-wt % base.

3. The method of claim 2, and where the aqueous base has a concentration of about 10-wt % base.

4. The method of claim 1, and where the aqueous hydrogen halide is selected from the group consisting of aqueous hydrogen chloride and aqueous hydrogen bromide.

5. The method of claim 4, and where the aqueous hydrogen halide has a concentration from about 20-wt % to about 36-wt % hydrogen halide.

6. The method of claim 1, and where no organic solvent is used to purify the intermediate prepared in step (a).

7. The method of claim 1, and where the base is selected from the group consisting of sodium hydroxide and potassium hydroxide.

8. The method of claim 1, and further including the steps of distilling the acetyl-propanol and the aqueous hydrogen halide to obtain a distillate having a 5-halo-2-pentanone portion and an aqueous portion and returning at least part of the aqueous portion to the still pot.

9. A method to prepare cyclopropyl methylketone, comprising:
   (a) reacting acetyl-propanol with an aqueous hydrogen halide to produce an intermediate; and
   (b) reacting the intermediate with an aqueous base to produce cyclopropyl methylketone without previously isolating the intermediate with an organic solvent, said base having a concentration from about 5-wt % to about 15-wt % base.

10. The method of claim 9, and where the aqueous base has a concentration of about 10-wt %.

11. The method of claim 9, and where the aqueous hydrogen halide is selected from the group consisting of aqueous hydrogen chloride and aqueous hydrogen bromide.

12. The method of claim 9, and where the aqueous hydrogen halide has a concentration from about 20-wt % to about 36-wt % hydrogen halide.

13. The method of claim 9, and where the base is selected from the group consisting of sodium hydroxide and potassium hydroxide.

14. The method of claim 9, and further including the steps of distilling the acetyl-propanol and the aqueous hydrogen halide to obtain a distillate having a 5-halo-2-pentanone portion and an aqueous portion and returning at least part of the aqueous portion to the still pot.

15. A method to prepare cyclopropyl methylketone, comprising:
   (a) forming a mixture of acetyl-propanol and an aqueous hydrogen halide;
   (b) distilling the mixture to obtain a distillate having a 5-halo-2-pentanone portion and an aqueous portion and returning at least part of the aqueous portion to the distilland;
   (c) recovering 5-halo-2-pentanone from the distillate obtained in step (b); and
   (d) reacting the 5-halo-2-pentanone with an aqueous base having a concentration from about 5-wt % to about 15-wt % base to produce cyclopropyl methylketone.

16. The method of claim 15, and where the aqueous base has a concentration of about 10-wt % base.

17. The method of claim 15, and where the aqueous hydrogen halide is selected from the group consisting of aqueous hydrogen chloride and aqueous hydrogen bromide.

18. The method of claim 17, and where the aqueous hydrogen halide has a concentration from about 20-wt % to about 36-wt % hydrogen halide.

19. The method of claim 15, and where no organic solvent is utilized to isolate the cyclopropyl methylketone.

20. The method of claim 15, and where the base is selected from the group consisting of sodium hydroxide and potassium hydroxide.

21. The method of claim 20, and where the aqueous base has a concentration of about 10-wt % base.

22. The method of claim 1, and where step (b) is performed between 30° C. and 40° C.

23. The method of claim 9, and where step (b) is performed between 30° C. and 40° C.

24. The method of claim 15, and where step (d) is performed between 30° C. and 40° C.

* * * * *